US011213538B2

(12) United States Patent
Asai et al.

(10) Patent No.: US 11,213,538 B2
(45) Date of Patent: Jan. 4, 2022

(54) AGENT FOR OVERCOMING IMMUNOSUPPRESSION AND USE THEREOF

(71) Applicants: GENERAL INCORPORATED ASSOCIATION PHARMA VALLEY PROJECT SUPPORTING ORGANIZATION, Mishima (JP); KABUSHIKI KAISHA YAKULT HONSHA, Minato-ku (JP)

(72) Inventors: Akira Asai, Shizuoka (JP); Naohisa Ogo, Shizuoka (JP); Daisuke Muraoka, Nagasaki (JP); Hiroshi Shiku, Tsu (JP); Naozumi Harada, Tsu (JP)

(73) Assignees: GENERAL INCORPORATED ASSOCIATION PHARMA VALLEY PROJECT SUPPORTING ORGANIZATION, Mishima (JP); KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

(21) Appl. No.: 16/073,871

(22) PCT Filed: Feb. 15, 2017

(86) PCT No.: PCT/JP2017/005566
§ 371 (c)(1),
(2) Date: Jul. 30, 2018

(87) PCT Pub. No.: WO2017/141981
PCT Pub. Date: Aug. 24, 2017

(65) Prior Publication Data
US 2019/0038645 A1 Feb. 7, 2019

(30) Foreign Application Priority Data
Feb. 16, 2016 (JP) .............................. JP2016-026745

(51) Int. Cl.
*A61K 31/704* (2006.01)
*A61K 35/17* (2015.01)
*A61P 35/00* (2006.01)
*A61P 37/02* (2006.01)
*A61K 45/00* (2006.01)
*A61K 39/00* (2006.01)
*A61K 45/06* (2006.01)

(52) U.S. Cl.
CPC ............ *A61K 31/704* (2013.01); *A61K 35/17* (2013.01); *A61K 39/00* (2013.01); *A61K 45/00* (2013.01); *A61K 45/06* (2013.01); *A61P 35/00* (2018.01); *A61P 37/02* (2018.01)

(58) Field of Classification Search
CPC ........ A61K 8/355; A61K 8/40; A61K 31/122; A61K 31/704; A61P 35/00; A61P 37/00; A61P 37/04

See application file for complete search history.

(56) References Cited

U.S. PATENT DOCUMENTS

2008/0214452 A1    9/2008   Obeid

FOREIGN PATENT DOCUMENTS

| CN | 103156871 A | * | 6/2013 |
| CN | 103717619 A | | 4/2014 |
| JP | 2-200637 A | | 8/1990 |
| JP | 2010-502681 A | | 1/2010 |

OTHER PUBLICATIONS

Tongu, M. et al., Cancer Immunol Immunother. vol. 59 pp. 769-777. Published 2010. (Year: 2010).*
Hebishima et al (Exp. Anim vol. 60 pp. 101-109. Published 2011). (Year: 2011).*
Fang Li et al., (Asian Pacific J. Cancer. Prev. vol. 14 pp. 1721-1724 published 2013) (Year: 2013).*
Mattarollo et al., (Cancer Research vol. 71 pp. 4809-4820 Published 2011) (Year: 2011).*
Zhang et al., (Cancer Letters vol. 369 pp. 331-335 published online Dec. 28, 2015) (Year: 2015).*
Epirubicin. Pubchem. Published 2020. (Year: 2020).*
Janinis et al., Tumori vol. 86 pp. 37-41. Published 2000. (Year: 2000).*
Todorova et al., Biotechnology and Biotechnological Equipment vol. 19 pp. 132-135. Published 2005. (Year: 2005).*
Lin et al (Nuclear Medicine and Biology vol. 40 pp. 437-441. Published 2013) (Year: 2013).*
Lin (Nuclear Medicine and Biology vol. 40 pp. 437-441. Published 2013). (Year: 2013).*
Todorova (Biotechnology and Biotechnological Equipment vol. 19 p. 132-135. Published 2005) (Year: 2005).*
Kudo (Liver Cancer vol. 4 pp. 201-207. Published 2015) (Year: 2015).*
Noelia Casares, et al., "A Peptide Inhibitor of FOXP3 Impairs Regulatory T Cell Activity and Improves Vaccine Efficacy in Mice," The Journal of Immunology, 2010, vol. 185, pp. 5150-5159.
Nicolas Larmonier, et al., "Imatinib Mesylate Inhibits CD4+CD25+ Regulatory T Cell Activity and Enhances Active Immunotherapy against BCR-ABL−Tumors[1]," The Journal of Immunology, vol. 181, 2008, pp. 6955-6963.
Lan-Fang Li, et al., "Epirubicin Inhibits Soluble CD25 Secretion by Treg Cells Isolated from Diffuse Large B-cell Lymphoma Patients," Asian Pacific Journal of Cancer Prevention, vol. 14, No. 3, 2013, pp. 1721-1724.
Jonathan Rios-Doria, et al., "Doxil Synergizes with Cancer Immunotherapies to Enhance Antitumor Responses in Syngeneic Mouse Models," Neoplasia, vol. 17, No. 8, Aug. 2015, pp. 661-670.

(Continued)

*Primary Examiner* — Theodore R. Howell
*Assistant Examiner* — George W Kosturko
(74) *Attorney, Agent, or Firm* — Oblon, McClelland, Maier & Neustadt, L.L.P.

(57) ABSTRACT

To provide an agent for overcoming immunosuppression which can overcome immunosuppression by regulatory T cells. An agent for overcoming immunosuppression and an inhibitor of FOXP3 function containing an anthracycline antibiotic as an active ingredient.

4 Claims, 3 Drawing Sheets

(56) References Cited

OTHER PUBLICATIONS

Fei-Ting Hsu, et al., "Enhancement of adoptive T cell transfer with single low dose pretreatment of doxorubicin or paclitaxel in mice," Oncotarget, vol. 6, No. 42, 2015, pp. 44134-44150.

Noelia Casares, et al., "Caspase-dependent immunogenicity of doxorubicin-induced tumor cell death," The Journal of Experimental Medicine, vol. 202, No. 12, Dec. 19, 2005, pp. 1691-1701.

International Search Report dated Apr. 18, 2017 in PCT/JP2017/005566 filed Feb. 15, 2017.

Extended European Search Report dated Jul. 23, 2019 in European Patent Application No. 17753237.1, 7 pages.

Fucikova, J., et al., "Human Tumor Cells Killed by Anthracyclines Induce a Tumor-Specific Immune Response", Cancer Research, May 20, 2011, vol. 71. No. 14, XP055604997, pp. 4821-4833 with cover page.

Ladoire, S., et al., "FOXP3 expression in cancer cells and anthracyclines efficacy in patients with primary breast cancer treated with adjuvant chemotherapy in the phase III UNICANCER-PACS 01 trial", Annals of Oncology, vol. 23, No. 10, Oct. 2012,XP055605005, pp. 2552-2561.

Kashima, H., et al., "Epirubicin, Identified Using a Novel Luciferase Reporter Assay for Foxp3 Inhibitors, Inhibits Regulatory T Cell Activity", PLoS One, Jun. 10, 2016; vol. 11, No. 6, XP055604910, pp. 1-12.

Office Action dated Dec. 19, 2019, in Chinese Patent Application No. 201780011726.7 w/Machine translation.

\* cited by examiner

[Fig. 1]
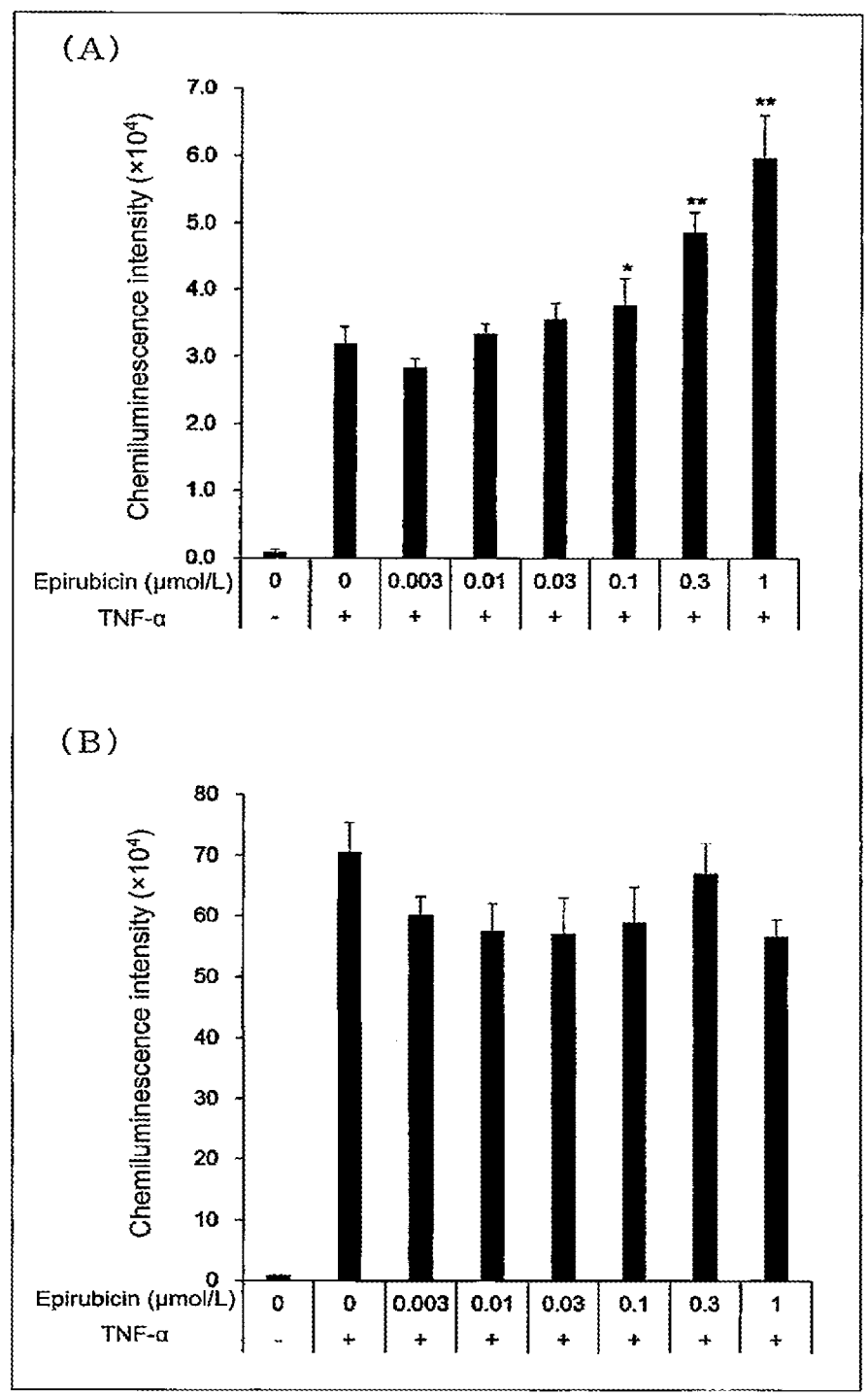

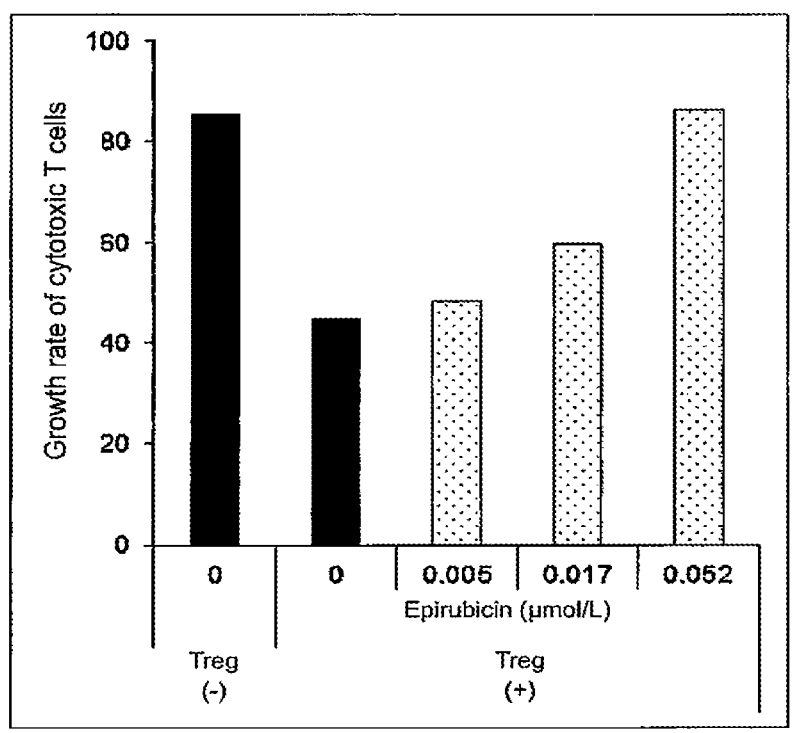
[Fig. 2]

[Fig. 3]
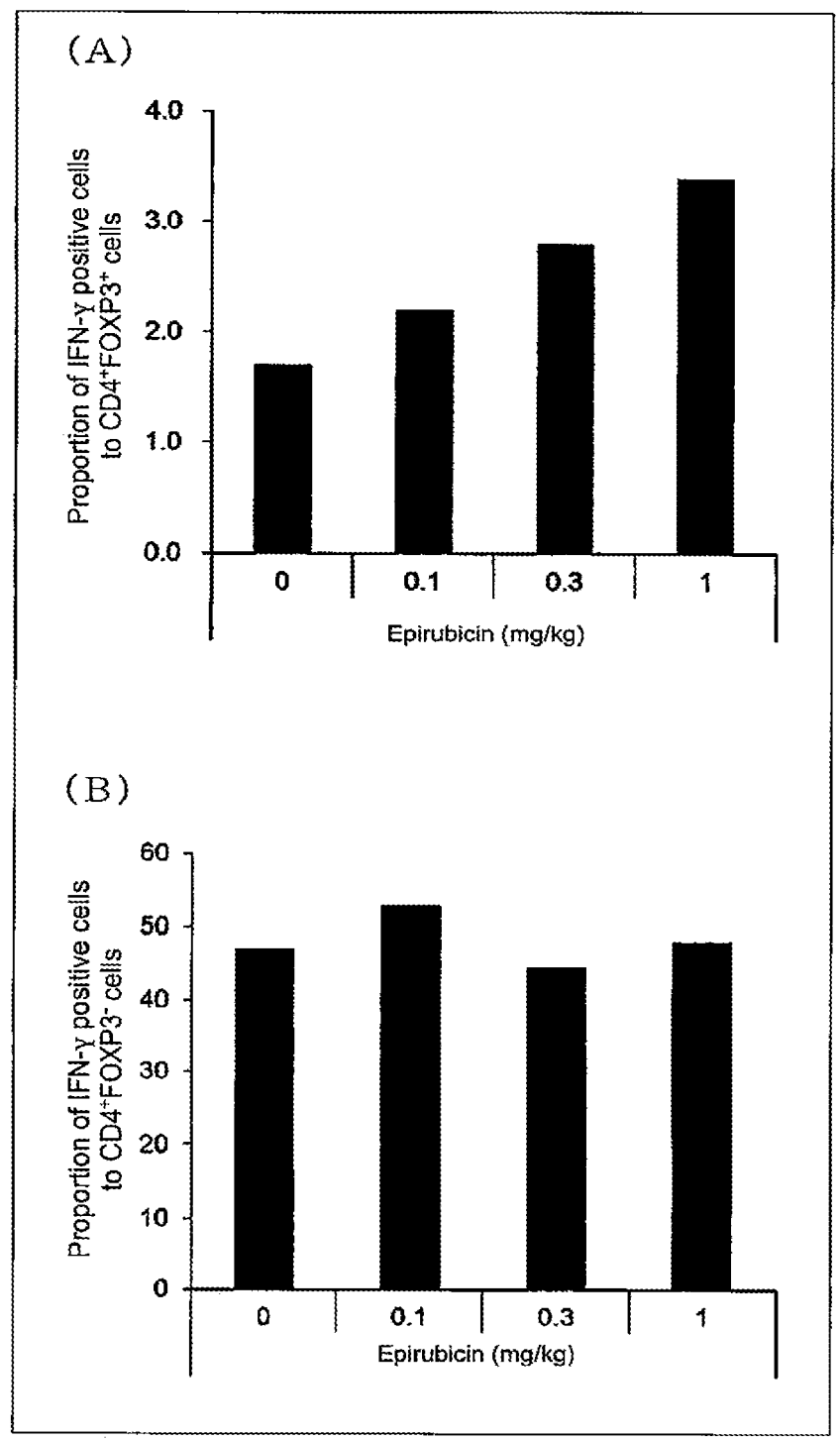

AGENT FOR OVERCOMING IMMUNOSUPPRESSION AND USE THEREOF

TECHNICAL FIELD

The present invention relates to an agent for overcoming immunosuppression, which can overcome immunosuppression by regulatory T cells, and use thereof.

BACKGROUND ART

Regulatory T cells (hereinafter also referred to as "Treg") are T cells which are responsible for suppressive control of immune responses in the immune systems, and play important roles for a brake to suppress excessive immune responses (negative control mechanism) and for maintaining immune homeostasis.

In the meantime, the immunosuppressive activity of regulatory T cells suppresses the induction of immune responses when cancer is developed or infectious bacteria enter the body. For example, it has become clear that regulatory T cells suppress the function of tumor-reactive T cells in vitro and the accumulation of regulatory T cells has a poor prognosis in various types of cancer. Therefore, various attempts to control the function of regulatory T cells have been made in cancer immunotherapy.

It has been confirmed that FOXP3 is expressed in regulatory T cells. It is thought that FOXP3 is a main transcription factor for regulatory T cells, and FOXP3 has a function to control immunosuppression by regulatory T cells. Therefore, there is a possibility that a substance which inhibits FOXP3 function can overcome immunosuppression by regulatory T cells and can be used for cancer immunotherapy and the like.

As the substance which inhibits FOXP3 function, for example, Peptide P60 (Non patent Literature 1) and imatinib (Non patent Literature 2) have been known.

In the meantime, anthracycline antibiotics are a group of compounds which are derived from a *Streptomyces* microorganism and are used for cancer chemotherapy, and have been used for the treatment of many cancers including leukemia, lymphoma, breast cancer, uterus cancer, ovarian cancer and lung cancer. However, it has been completely unknown that such anthracycline antibiotics have an inhibitory action of FOXP3 function and an action of overcoming immunosuppression by regulatory T cells.

CITATION LIST

Non Patent Literature

Non patent Literature 1: Casares N, et. al., J Immunol. 185:5150-59, 2010
Non patent Literature 2: Larmonier N, et. al., J Immunol. 181: 6955-6963, 2008

SUMMARY OF INVENTION

Technical Problem

The present invention relates to the provision of an agent for overcoming immunosuppression, which can overcome immunosuppression by regulatory T cells.

Solution to Problem

As a result of investigations on compounds which regulate immunosuppression by regulatory T cells, it was found that anthracycline antibiotics including epirubicin have an action of inhibiting FOXP3 function and can overcome immunosuppression by regulatory T cells.

That is, the present invention relates to the following 1) to 18).

1) An agent for overcoming immunosuppression, comprising an anthracycline antibiotic as an active ingredient.
2) An inhibitor of FOXP3 function, comprising an anthracycline antibiotic as an active ingredient.
3) The agent for overcoming immunosuppression according to 1) or the inhibitor of FOXP3 function according to 2), wherein the anthracycline antibiotic is one or more selected from the group consisting of epirubicin, doxorubicin, pirarubicin, daunorubicin, idarubicin, and a salt thereof.
4) The agent for overcoming immunosuppression according to 1) or the inhibitor of FOXP3 function according to 2), wherein the anthracycline antibiotic is epirubicin or a salt thereof.
5) The agent for overcoming immunosuppression according to 1) or the inhibitor of FOXP3 function according to 2), wherein the anthracycline antibiotic is administered at a lower dose than a dose showing cytotoxicity against cancer cells.
6) The agent for overcoming immunosuppression or inhibitor of FOXP3 function according to 5), which is administered at a lower dose than a dose showing cytotoxicity against solid cancer and/or blood cancer.
7) The agent for overcoming immunosuppression or inhibitor of FOXP3 function according to 5) or 6), which is administered at 0.01 to 1 mg/kg per day as an anthracycline antibiotic.
8) The agent for overcoming immunosuppression or inhibitor of FOXP3 function according to 5) or 6), which is administered at $\frac{1}{100}$ to $\frac{4}{5}$ of a dose showing cytotoxicity against solid cancer and/or blood cancer as an anthracycline antibiotic.
9) The agent for overcoming immunosuppression or inhibitor of FOXP3 function according to 1) to 8), which is used in combination with another anticancer therapy.
10) The agent for overcoming immunosuppression or inhibitor of FOXP3 function according to 9), wherein another anticancer therapy is cancer chemotherapy or cancer immunotherapy.
11) The agent for overcoming immunosuppression or inhibitor of FOXP3 function according to 10), wherein the cancer immunotherapy is immune checkpoint blockade therapy, cancer vaccine therapy, or T cell transfer therapy.
12) A medicine comprising an anthracycline antibiotic in an amount of 0.01 to 4 mg.
13) An anthracycline antibiotic for use as an agent for overcoming immunosuppression.
14) An anthracycline antibiotic for use as an inhibitor of FOXP3 function.
15) Use of an anthracycline antibiotic for producing an agent for overcoming immunosuppression.
16) Use of an anthracycline antibiotic for producing an inhibitor of FOXP3 function.
17) A method for overcoming immunosuppression, comprising administering an effective amount of an anthracycline antibiotic to a patient.
18) A method for inhibiting FOXP3 function, comprising administering an effective amount of an anthracycline antibiotic to a patient.

Advantageous Effects of Invention

According to the present invention, it is possible to provide a pharmaceutical product useful for inhibiting FOXP3 function and for overcoming immunosuppression by regulatory T cells. According to the agent for overcoming immunosuppression or inhibitor of FOXP3 function of the present invention, for example, tumor immunity can be activated by overcoming tumor immunosuppression and a therapeutic effect on tumors can be obtained.

BRIEF DESCRIPTION OF DRAWINGS

FIG. 1 shows a FOXP3 function inhibitory activity of epirubicin. (A) shows an activity when HEK293/NF-κB-RE/FOXP3 cells were used, and (B) shows an activity when HEK293/NF-κB-RE cells were used.

FIG. 2 shows an action of epirubicin for overcoming immunosuppression by mouse regulatory T cells, and shows a growth rate of $CD8^+$ T cells which are cytotoxic T cells.

FIG. 3 shows changes in function of mouse regulatory T cells by epirubicin. (A) shows a proportion of the number of IFN-γ positive cells to the number of $CD4^+FOXP3^+$ cells, and (B) shows a proportion of the number of IFN-7 positive cells to the number of $CD4^+FOXP3^-$ cells.

DESCRIPTION OF EMBODIMENTS

In the present invention, anthracycline antibiotics include anthracycline compounds known as antitumor agents such as doxorubicin, idarubicin, epirubicin, daunorubicin, pirarubicin, amrubicin, aclacinomycin, anthramycin, zorubicin, and salts thereof. Among them, epirubicin, doxorubicin, pirarubicin, daunorubicin, and idarubicin are preferred, and epirubicin is more preferred.

The salts are not particularly limited as long as they are pharmaceutically acceptable salts, and examples thereof include salts of inorganic acids and organic acids such as hydrochloric acid, hydrobromic acid, sulfuric acid, phosphoric acid, methanesulfonic acid, trifluoromethanesulfonic acid, benzenesulfonic acid, p-toluenesulfonic acid, acetic acid, trifluoroacetic acid, malic acid, tartaric acid, citric acid, lactic acid, oxalic acid, succinic acid, fumaric acid, maleic acid, benzoic acid, and salicylic acid, and among them, a hydrochloric acid salt is preferred.

The anthracycline antibiotics can be obtained by isolation from a *Streptomyces* microorganism or by a known synthetic method. Alternatively, a commercially available pharmaceutical product may also be used.

As described in Examples given below, in cells obtained by stably introducing FOXP3 gene into HEK293/NF-κB-RE cells, TNF-α activates NF-κB and luciferase is expressed along with NF-κB, while anthracycline antibiotics such as epirubicin, daunorubicin, doxorubicin, pirarubicin, and idarubicin have actions of inhibiting FOXP3 function, activating NF-κB, and moreover causing an increase in the expression of luciferase.

The FOXP3 gene encodes a transcription factor, and is thought to be a master gene which controls the differentiation and action of regulatory T cells having an immunosuppressive action (Williams L M, et. al., Nat. Immunol. 8:277-284, 2007). Therefore, inhibiting FOXP3 function can suppress the development and function of regulatory T cells and moreover can overcome immunosuppression by regulatory T cells. Practically, epirubicin enables overcoming an immunosuppressive action of regulatory T cells at a lower concentration than an already known concentration which shows a sufficient antitumor effect.

Therefore, the anthracycline antibiotics can be used as an inhibitor of FOXP3 function which suppresses the function of FOXP3 gene and an agent for overcoming immunosuppression which overcomes immunosuppression by regulatory T cells.

Herein, the "regulatory T cells" mean T cells which have a function of suppressing abnormal or excessive immune responses and are responsible for immune tolerance. In the present invention, the regulatory T cells typically include CD4-positive FOXP3-positive T cells ($CD4^+FOXP3^+Treg$).

In the present invention, the "inhibition of FOXP3 function" means inhibiting the function of FOXP3 as a transcription factor, and it does not matter whether the inhibition method is direct or indirect to FOXP3. For example, the "inhibition of FOXP3 function" encompasses inhibiting the interaction of FOXP3 and another protein.

Herein, the activity of inhibiting FOXP3 function can be evaluated by preparing HEK293 cells (HEK293/NF-κB-RE cells) into which a luciferase reporter vector has been stably introduced and cells (HEK293/NF-κB-RE/FOXP3 cells) obtained by stably introducing the FOXP3 gene into the HEK293/NF-κB-RE cells, adding a test drug and TNF-alpha (TNF-α) thereto, followed by culture, and measuring a difference in chemiluminescence intensity in each cell group.

In the present invention, the "overcoming immunosuppression" means overcoming the control of immune responses suppressed by regulatory T cells to thereby induce immune responses. Many of the mechanisms which suppress antitumor immunity are thought to be a result of the activation of regulatory T cells. Therefore, overcoming the control of immune responses by reducing the number of regulatory T cells or weakening the suppressive ability thereof induces tumor immune responses, and a tumor can be therapeutically removed, or tumor functions can be inactivated.

In recent years, the therapeutic effect on Alzheimer's disease by overcoming immunosuppression has also been reported (Nature Medicine 22: 135-137, 2016), and an agent for overcoming immunosuppression can also be applied to the treatment of Alzheimer's disease.

The agent for overcoming immunosuppression and inhibitor of FOXP3 function of the present invention (hereinafter, referred to as an "agent for overcoming immunosuppression, etc.") are used in the form of a pharmaceutical product or as a material which is blended in a pharmaceutical product. The preparation form in this case is not particularly limited and can be suitably selected depending on therapeutic purposes. Specific examples thereof include oral agents (tablet, coated tablet, powder, granule, capsule, liquid, etc.), injection, suppository, patch, and ointment.

Such pharmaceutical preparations can be prepared using an anthracycline antibiotic and a pharmacologically acceptable carrier by a conventionally known method. Various types of carrier which are widely used for common drugs are used as such a carrier, and examples thereof include an excipient, a binder, a disintegrating agent, a lubricant, a diluent, a solubilizing agent, a suspending agent, a tonicity agent, a pH adjuster, a buffer, a stabilizing agent, a colorant, a flavoring agent, and a corrigent.

Examples of the excipient include lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerin, sodium alginate, gum Arabic, and mixtures thereof. Examples of the lubricant include purified talc, stearates, borax, polyethylene glycol, and mixtures thereof. Examples of the binder include simple syrup, glucose solution, starch solution, gelatin solution, polyvinyl alcohol, polyvinyl ether, polyvinylpyrrolidone, carboxymethylcellulose, shellac, methylcellulose, ethylcellulose, water, ethanol, potassium phosphate, and mixtures thereof. Examples of the disintegrating agent include dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch, lactose, and mixtures thereof. Examples of the diluent include water, ethyl alcohol, macrogol, propylene glycol, ethoxylated isostearyl alcohol, polyoxylated isostearyl alcohol, polyoxyethylene sorbitan fatty acid esters, and mixtures thereof. Examples of the stabilizing agent include sodium pyrosulfite, ethylenediaminetetraacetic acid, thioglycolic acid, thiolactic acid, and mixtures thereof. Examples of the tonicity agent include sodium chloride, boric acid, glucose, glycerin, and mixtures thereof. Examples of the pH adjuster and buffer include sodium citrate, citric acid, sodium acetate, sodium phosphate, and mixtures thereof. Examples of the soothing agent include procaine hydrochloride, lidocaine hydrochloride, and mixtures thereof.

It should be noted that the content of anthracycline antibiotic in the above pharmaceutical preparation is generally preferably 0.01 to 4 mg in the preparation and more preferably 0.1 to 1 mg.

The dose of the agent for overcoming immunosuppression, etc. of the present invention may be one where an anthracycline antibiotic can show an action of inhibiting FOXP3 function or an action of overcoming immunosuppression, and is preferably a dose where the cytotoxicity of the anthracycline antibiotic cannot be shown. In particular, the dose is preferably a lower dose than the dose of an anthracycline antibiotic normally used for solid cancer or blood cancer.

The dose is suitably set specifically depending on the age, disease stage, treatment history, etc. of patients, and is 0.01 to 1 mg/kg, preferably 0.1 to 0.25 mg/kg, per day as an anthracycline antibiotic. In addition, the dose can be 1/100 to 4/5, preferably 1/20 to 1/4, of a dose showing cytotoxicity against solid cancer or blood cancer.

It should be noted that subjects to which the agent for overcoming immunosuppression, etc. of the present invention are applied include humans in need of overcoming immunosuppression by regulatory T cells, and preferably humans in need of overcoming tumor immunosuppression and activating tumor immunity.

Herein, tumors are not particularly limited, and examples thereof include head and neck cancer, esophageal cancer, stomach cancer, colorectal cancer, liver cancer, gallbladder and bile duct cancer, pancreatic cancer, lung cancer, breast cancer, ovarian cancer, bladder cancer, prostate cancer, testicle cancer, bone and soft tissue sarcoma, malignant lymphoma, leukemia, cervical cancer, skin cancer, and brain tumor.

The agent for overcoming immunosuppression, etc, of the present invention can be administered alone; however, it is preferred that they be used in combination with another anticancer therapy.

When administered alone, the agent for overcoming immunosuppression, etc. of the present invention can be administered with the same concentration maintained or can be administered while changing the concentrations.

In addition, examples of another anticancer therapy include conventional cancer chemotherapy (cytotoxic chemotherapy) which is different from the present invention, surgical operations, radiation therapy, photodynamic therapy, and cancer immunotherapy.

Examples of the cancer chemotherapy include administration of an antitumor agent containing a compound with cytotoxicity.

Antitumor agents which can be used in combination are not particularly limited, and examples thereof include alkylating agents such as cyclophosphamide, ifosfamide, melphalan, busulfan, carboquone, and dacarbazine; antimetabolites such as 6-mercaptopurine, methotrexate, 5-fluorouracil, tegafur, enocitabine, and antifolate (pemetrexed, etc.); anticancer antibiotics such as actinomycin D, bleomycin, pepleomycin, mitomycin C, aclarubicin, and neocarzinostatin; plant alkaloids such as vincristine, vindesine, vinblastine, and taxane anticancer agents (taxotere, taxol, etc); and platinum compounds such as cisplatin, carboplatin, and oxaliplatin, and also include molecular target drugs such as imatinib, gefitinib, sorafenib, sunitinib, axitinib, vemurafenib, and trametinib. These can be used alone, or two or more of these can be used in combination. In addition, the agents for overcoming immunosuppression of the present invention can also be used in combination.

The combined administration with an antitumor agent means that the agent for overcoming immunosuppression, etc. of the present invention and an antitumor agent are administered as a single agent, and also means that the agent for overcoming immunosuppression, etc. of the present invention and an antitumor agent are administered simultaneously or separately with an interval as two agents. In the latter case, the frequency of administration of an antitumor agent and the agent for overcoming immunosuppression, etc. may be the same or different.

The cancer immunotherapy is not particularly limited, and examples thereof include immune checkpoint blockade therapy which inhibits the binding of PD-L1 (programmed death-ligand 1) and PD-L2 (programmed death-ligand 2), ligands expressed on cancer cells, and PD-1 (programmed death-1), a receptor on T cells, immune checkpoint blockade therapy which inhibits CTLA-4, a surface molecule of T cells, cancer vaccine therapy (peptide vaccine therapy, dendritic cell vaccine therapy, etc.), and T cell transfer therapy.

Examples of immune checkpoint inhibitors which are used for immune checkpoint blockade therapy include a human IgG4 monoclonal antibody against PD-1, and specifically include nivolumab and pembrolizumab.

The dose of the agent for overcoming immunosuppression, etc. of the present invention in a case where the agent for overcoming immunosuppression, etc. of the present invention is used in combination with another anticancer therapy can be a lower dose than the above-described dose.

EXAMPLES

Example 1 FOXP3 Function Inhibitory Activity of Epirubicin

1. Material
(a) Cells
i) HEK293/NF-κB-RE Cells (HEK293 Cells into which a Luciferase Reporter Vector has been Stably Introduced):

Into a human embryonic kidney-derived cell line HEK293 (RIKEN CELL BANK), pGL4.32 [luc2P/NF-κB-RE/Hygro] (Promega Corporation), which is a luciferase reporter vector, was introduced, and the cells were subjected to a selection through culture in a medium containing 0.2 mg/mL Hygromycin B for 3 weeks. The obtained single clone was isolated and established as a stable line. For culture, DMEM (Dulbecco's Modified Eagle's Medium) containing 10% heat inactivated FBS and 0.2 mg/mL Hygromycin B was used.

ii) HEK293/NF-κB-RE/FOXP3 Cells (Cells Obtained by Stably Introducing FOXP3 Gene into HEK293/NF-κB-RE Cells):

Into HEK293/NF-κB-RE cells, pcDNA3.1-FOXP3 (Department of Cancer vaccine therapy/Immuno-gene therapy, Mie University Graduate School of Medicine), which is a FOXP3 gene expression vector, was introduced, and the cells were subjected to a selection through culture in a medium containing 0.5 mg/mL G418 for 3 weeks. The obtained single clone was isolated and established as a stable line. For culture, DMEM containing 10% heat inactivated FBS, 0.2 mg/mL Hygromycin B, and 0.5 mg/mL G418 was used.

(b) Test Drug

Epirubicin manufactured by TOCRIS was used. The final concentration of epirubicin and the addition of TNF-alpha are shown in Table 1. As a control, cells to which epirubicin was not added and TNF-alpha was added were used.

TABLE 1

| | Epirubicin concentration (μM) | | | | | | |
|---|---|---|---|---|---|---|---|
| | 0 | 0 | 0.003 | 0.01 | 0.03 | 0.1 | 0.3 | 1 |
| Addition of TNF-α | − | + | + | + | + | + | + | + |

2. Method

A cell suspension of $1.875 \times 10^5$ cells/mL was prepared for HEK293/NF-κB-RE/FOXP3 cells and HEK293/NF-κB-RE cells, respectively, using DMEM with 10% heat inactivated FBS and without phenol red (medium for assay). The cell suspension was seeded into a 96 well white microplate (nunc) at 80 μL/well ($1.5 \times 10^4$ cells/well) and the cells were cultured overnight under the conditions of 37° C. and 5% $CO_2$.

A DMSO solution of a test drug with a concentration of 1000 times the final concentration was diluted 100 times with the medium for assay to prepare a test drug solution with a concentration of 10 times the final concentration (a 10 times concentration test drug solution). To each well into which the cell suspension was seeded, 10 μL of the 10 times concentration test drug solution was added and treatment was carried out under the conditions of 37° C. and 5% $CO_2$ for an hour (10 μL of a 1% DMSO solution was added to the control at this time).

Recombinant Human TNF-alpha (R&D Systems) was made to 100 μg/mL with 0.1% BSA-containing PBS, and was further diluted with the medium for assay to prepare a 3 ng/mL TNF-alpha solution. To each well described above, 10 μL of the 3 ng/mL TNF-alpha solution was added, and stimulation was performed under the conditions of 37° C. and 5% $CO_2$ for 2.5 hours (the final concentration of TNF-alpha: 0.3 ng/mL).

The culture supernatant was removed, and the cells were washed once with 100 μL of the medium for assay. After adding 100 μL of the medium for assay, 50 μL of Steady-Glo (Promega Corporation) was added. The microplate was shaken for 10 minutes on a plate shaker with the light blocked. After shaking, the chemiluminescence intensity was measured by ARVO Light plate reader (Perkin Elmer). It should be noted that each test was carried out three times. The results obtained by using HEK293/NF-κB-RE/FOXP3 cells are shown in FIG. 1(A) and the results obtained by using HEK293/NF-κB-RE cells are shown in FIG. 1(B).

3. Results

In the case of HEK293/NF-κB-RE/FOXP3 cells, the chemiluminescence intensity increased in an epirubicin concentration-dependent manner (FIG. 1(A)). In particular, in a solution which had been exposed to 0.1 μM epirubicin, the chemiluminescence intensity was significantly high as compared to that in the control at $P<0.05$. In a solution which had been exposed to 0.3 or 1 μM epirubicin, the chemiluminescence intensity was significantly high as compared to that in the control at $P<0.01$. On the other hand, in the case of HEK293/NF-κB-RE cells, concentration-dependent changes were not observed (FIG. 1(B)). From these results, it was confirmed that epirubicin selectively inhibited FOXP3 function.

Example 2 FOXP3 Function Inhibitory Activity of Anthracycline Antibiotics

The FOXP3 function inhibitory activity of a plurality of anthracycline antibiotics (epirubicin, pirarubicin, daunorubicin, doxorubicin, and idarubicin) was confirmed.

1. Material

The same HEK293/NF-κB-RE/FOXP3 cells and HEK293/NF-κB-RE cells, and epirubicin as in Example 1 were used.

As pirarubicin, daunorubicin, doxorubicin, and idarubicin, those manufactured by SIGMA ALDRICH were used.

2. Method

The FOXP3 inhibitory activity was evaluated in the same method as that in Example 1 except that the test drug was changed to epirubicin, pirarubicin, daunorubicin, doxorubicin, or idarubicin. The final concentration of each test drug was 0.01, 0.03, 0.1, 0.3 or 1 μM (only epirubicin and doxorubicin were tested also at 1 μM, and idarubicin was tested only at 0.01 and 0.03 μM).

The chemiluminescence intensity when DMSO (control) had been added in place of the test drug was considered as 1.0, and the chemiluminescence intensity was calculated as a multiple value. Furthermore, the chemiluminescence intensity ratio was calculated by the Formula 1 below. The test was carried out three times. The results are shown in Table 2.

Chemiluminescence intensity ratio=(chemiluminescence intensity measured when HEK293/NF-κB-RE/FOXP3 cells were used)/(chemiluminescence intensity measured when HEK293/NF-κB-RE cells were used) [Formula 1]

3. Results

FOXP3 inhibitory activity was observed for all the anthracycline antibiotics (Table 2). In particular, the activity of epirubicin increased in a concentration-dependent manner, and it was confirmed that epirubicin was the most preferred as a FOXP3 inhibitor.

TABLE 2

| Test drug concentration | Epirubicin | Pirarubicin | Daunorubicin | Doxorubicin | Idarubicin |
|---|---|---|---|---|---|
| 0.01 | 1.29 | 1.03 | 1.09 | 0.97 | 1.02 |
| 0.03 | 1.39 | 1.08 | 1.12 | 1.08 | 1.21 |
| 0.1 | 1.42 | 1.53 | 1.82 | 1.14 | ND |

TABLE 2-continued

| Test drug concentration | Epirubicin | Pirarubicin | Daunorubicin | Doxorubicin | Idarubicin |
|---|---|---|---|---|---|
| 0.3 | 1.62 | 1.50 | 2.07 | 1.29 | ND |
| 1 | 2.37 | ND | ND | 1.38 | ND |

ND: no data

Example 3 Overcoming Immunosuppressive Action of Mouse Regulatory T Cells by Epirubicin-1

(1) Material

BALB/c mice were purchased from Japan SLC, Inc.

(2) Method

Anti-CD3 antibody (1 μg/mL, manufactured by eBioscience) was added to a 12 well flat-bottom plate and the plate was left to stand at 4° C. overnight, and then washed with RPMI 1640 medium. Spleen was isolated from BALB/c mice, and CD4$^+$CD25$^+$ T lymphocytes were isolated using a mouse regulatory T cell isolation kit (manufactured by Miltenyi Biotec) and autoMACS separator (manufactured by Miltenyi Biotec). To the 12 well flat-bottom plate coated with anti-CD3 antibody, seven hundred thousand CD4$^+$CD25$^+$ T lymphocytes per well were added, and anti-CD28 antibody (manufactured by eBioscience) and IL-2 (NOVARTIS) were added so that the concentrations were 1 μg/mL and 60 IU/mL, respectively. Next, epirubicin was added at various concentrations and the lymphocytes were cultured in an incubator at 37° C. for 48 hours and then washed with a 10% FBS supplemented RPMI 1640 medium.

Anti-CD3 antibody (1 μg/mL, manufactured by eBioscience) was added to a 96 well flat-bottom plate and the plate was left to stand at 4° C. overnight, and then washed with RPMI 1640 medium. Spleen was isolated from BALB/c mice and CD8$^+$ T lymphocytes were isolated using a mouse CD8$^+$ T cell isolation kit (manufactured by Miltenyi Biotec) and autoMACS separator (manufactured by Miltenyi Biotec). The lymphocytes were stained with carboxyfluorescein succinimidyl ester (CFSE) and then washed. To the 96 well flat-bottom plate coated with anti-CD3 antibody, forty thousand CD8$^+$ T lymphocytes per well were added, and forty thousand CD4$^+$CD25$^+$ T lymphocytes described above per well were further added. Anti-CD28 antibody (manufactured by eBioscience) was added in a concentration of 1 μg/mL and the lymphocytes were cultured in an incubator at 37° C. for 72 hours. The lymphocytes were collected and washed with PBS containing 0.5% BSA, and then stained with anti-CD8-APC antibody (manufactured by eBioscience) and analyzed using FACS Canto II flow cytometer (manufactured by Becton Dickinson).

(3) Results

The growth rate of CD8$^+$ T cells (cytotoxic T cells) had a high value in the absence of regulatory T cells, while the growth rate decreased by about 40% in the presence of regulatory T cells (FIG. 2). However, when epirubicin was added at a low dose not showing cytotoxicity, the growth rate of CD8$^+$ T cells increased in a concentration-dependent manner (FIG. 2). From the results in Example 3, it was revealed that addition of epirubicin at a low dose overcome an immunosuppressive action of regulatory T cells.

Example 4 Overcoming Immunosuppressive Action of Mouse Regulatory T Cells by Epirubicin-2

(1) Material

BALB/c mice were purchased from Japan SLC, Inc. CMS5a cells were obtained from Memorial Sloan Kettering Cancer Center.

(2) Method

CMS5a cells were transplanted under the skin in the posterodorsal region of female BALB/c mice (8 mice per group) on day 0. Epirubicin (0.1, 0.3, 1 mg/kg) or saline was administered intravenously on days 3, 5, and 7 (epirubicin does not show an anticancer action in such concentrations). On day 8, the mice were euthanized and tumors were collected. Using gentle MACS dissociator (manufactured by Miltenyi Biotec) in accordance with the instruction manual, tumor-infiltrating lymphocytes (TIL) were separated from the tumors. The collected cells were seeded into a 24 well plate and stimulated with phorbol 12-myristate 13-acetate (PMA) and ionomycin under the condition of 37° C. for an hour, and then cultured with GolgiPlug (BD Biosciences) for 6 hours. After collecting the cells, the cells were stained with PreCP-CyTM5.5 rat anti-mouse CD4 antibody (manufactured by BD Pharmingen) and V500 rat anti-mouse CD8a antibody (manufactured by BD Horizon) under the condition of 4° C. for 15 minutes. The stained cells were fixed with Fixation/Permeabilization Concentrate and Diluent (1:3, manufactured by eBioscience) under the condition of 4° C. overnight. After washing, Permeabilization buffer (manufactured by eBioscience) was added, and the fixed cells were stained with PE conjugated anti-mouse/rat FOXP3 (manufactured by eBioscience), anti-mouse IFN-γ-APC (manufactured by eBioscience) and PE conjugated anti-mouse IL-2 (manufactured by BioLegend) antibodies. The stained cells were analyzed using FACS Canto II flow cytometer (manufactured by Becton Dickinson).

(3) Results

The proportion of the number of IFN-γ positive cells to the number of CD4$^+$FOXP3$^+$ cells or CD4$^+$FOXP3$^-$ cells is shown in FIGS. 3(A) and (B), respectively. In the CD4$^+$FOXP3$^-$ group, the proportion of IFN-γ positive cells did not vary depending on the administration of epirubicin, while in the CD4$^+$FOXP3 group, the proportion of IFN-γ positive cells increased in a concentration-dependent manner, showing that immunity was activated.

It was revealed that, from the results of Examples 1 to 3, FOXP3 function was inhibited and an immunosuppressive action of regulatory T cells was overcome in vitro by epirubicin at a low dose and that, from the results of Example 4, IFN-γ, an inflammatory cytokine, was produced in vivo by the administration of epirubicin at a low dose, and thus it was revealed that immunity was activated.

The invention claimed is:

1. A method for overcoming immunosuppression by regulatory T cells, the method comprising administering to a patient epirubicin or a salt thereof, in a dose range of 0.1 mg/kg to 0.25 mg/kg, wherein the patient has a solid cancer.

2. The method of claim 1, further comprising another anticancer therapy.

3. The method of claim 2, wherein the another anticancer therapy is a cancer chemotherapy or a cancer immunotherapy.

4. The method of claim 3, wherein the another anticancer therapy is a cancer immunotherapy selected from the group consisting of an immune checkpoint blockade therapy, a cancer vaccine therapy, and a T cell transfer therapy.

* * * * *